United States Patent [19]

Chastain, Jr. et al.

[11] 4,264,470
[45] Apr. 28, 1981

[54] SELECTING GOAT ERYTHROCYTES TO SIMULATE HUMAN PLATELETS IN HEMATOLOGIC REFERENCE CONTROLS

[75] Inventors: David L. Chastain, Jr., Fort Lauderdale; Harold R. Crews, Miami; Stephen L. Ledis, Hialeah, all of Fla.

[73] Assignee: Coulter Electronics, Inc., Hialeah, Fla.

[21] Appl. No.: 36,795

[22] Filed: May 7, 1979

[51] Int. Cl.³ .................... G01N 33/48; G01N 35/00
[52] U.S. Cl. ........................................ 252/408; 424/3; 424/9; 424/12; 435/2
[58] Field of Search ............. 424/3, 9, 12, 101, 2; 435/2; 252/408

[56] References Cited

U.S. PATENT DOCUMENTS

| | | | |
|---|---|---|---|
| 3,553,310 | 1/1971 | Csizmas | 424/2 |
| 4,157,383 | 6/1979 | Sedlacek | 424/3 |
| 4,160,644 | 7/1979 | Ryan | 424/3 |
| 4,179,398 | 12/1979 | Hunt | 424/2 X |

Primary Examiner—Anna P. Fagelson
Attorney, Agent, or Firm—Meredith P. Sparks; Gerald R. Hibnick

[57] ABSTRACT

A method is described for preparing a human platelet analog for use as a reference control in particle analysis instrumentation of the Coulter type. Goat erythrocytes from individual goats which have been selected with respect to age, sex, selective breeding, a controlled environment, prior veterinary treatment, and diet are altered in size and/or combined with samples from several goats, as needed, to obtain a blend for use as a reference control for automated particle counting equipment in which the goat erythrocytes simulate in number, size and distribution the platelets in human whole blood. The controls are useful as a free-standing reference for determination of human platelets only, or can be added to whole blood reference controls for multi-parameter instruments.

11 Claims, 5 Drawing Figures

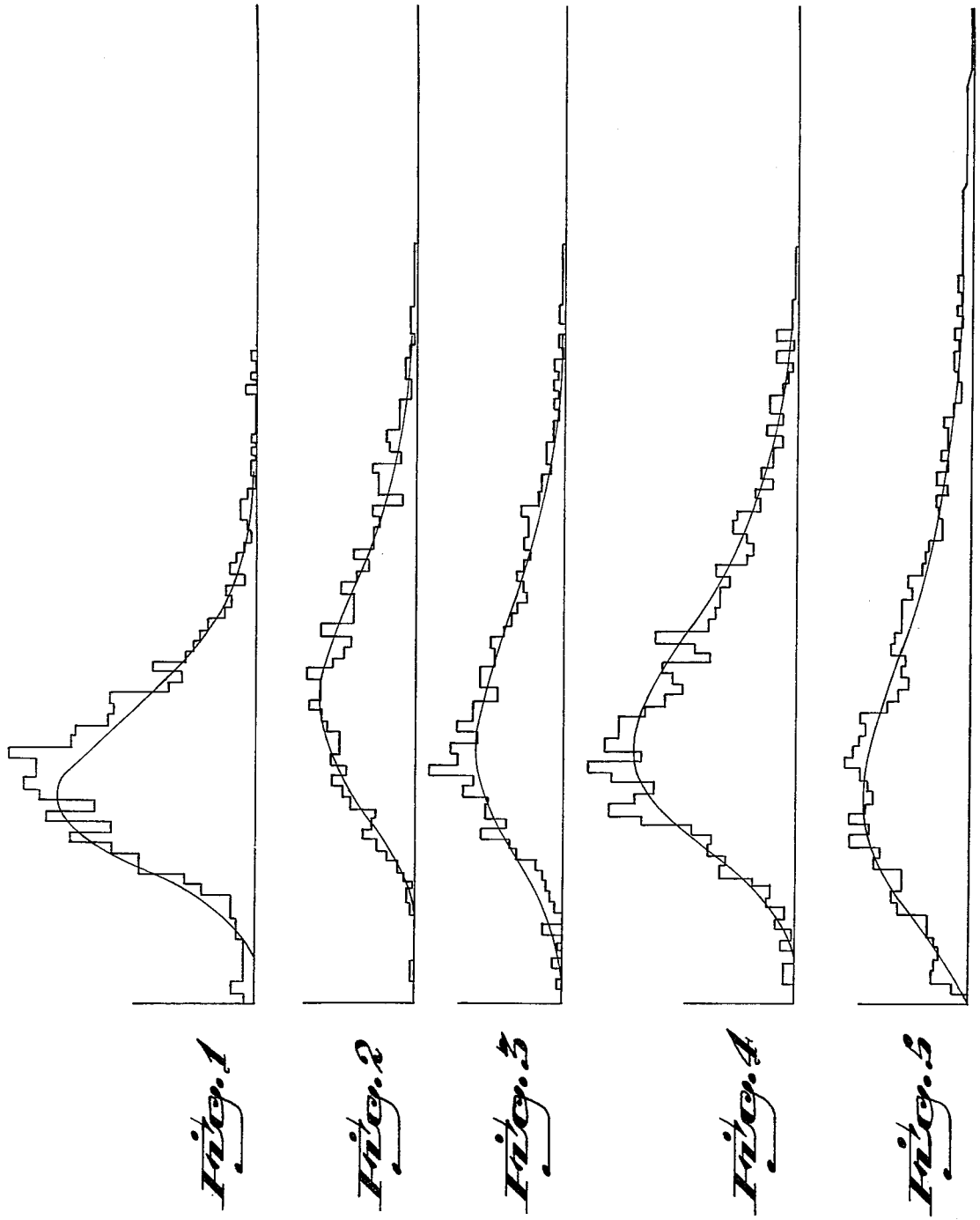

SELECTING GOAT ERYTHROCYTES TO SIMULATE HUMAN PLATELETS IN HEMATOLOGICAL REFERENCE CONTROLS

BACKGROUND OF THE INVENTION

This invention relates to a human platelet analog for use as a reference control in automated particle counting instrumentation of the Coulter type, and by microscope techniques.

Whole blood hematological reference control compositions are now made from stabilized human erythrocytes, preserved human erythrocytes as leukocyte analogs, and stabilized human platelets. Human platelets (thrombocytes) are round or oval disks, about ⅓ to ½ the diameter of the erythrocytes (red blood cells) found in human blood. They contain no hemoglobin (red coloring matter) and normally number from 150,000 to 350,000 per mm$^3$ in normal whole blood.

Previously available reference control products for checking the performance characteristics of particle analysis instruments for determining platelet parameters have suffered from the disadvantage of limited availability or high cost of human blood platelets and the disadvantage of poor stability and/or inconvenient methods of use, especially for automated particle counting instruments. Commercial experience has clearly indicated that the use of human platelets is beset with serious manufacturing cost, and a concern for the use of human blood resources for in vitro diagnostic products which might be contrary to a need to develop a national voluntary blood donor program.

A control product must accurately indicate on a comparative basis what a test sample of blood constitutes in a particular determination. Furthermore, it is evident how important it is for the control product to simulate blood collected in commonly used anticoagulants. For example, if the control product contains cells which are larger in size, the experimental result may be inaccurate in many types of automated equipment, if not almost meaningless.

Any system for automated platelet counting which distinguishes human platelets from other cells in the blood on the basis of the characteristic size range and volume distribution of platelets requires that the reference control material used as such closely simulates the size range and volume distribution characteristics of platelets in normal human blood. A reference control containing platelets or simulated platelets which has a narrow size distribution range would not be useful to determine whether the size distribution limits, between which the instrument counted "platelets", were correctly set. Both the upper and lower size limits of platelets must be represented in the reference control material. In addition, the mean platelet volume of the reference control material should be very close to that of normal human platelets. When upper and lower size limits and mean platelet volume are thus specified, it becomes a virtual necessity for the volume distribution histogram of the platelet material to approximate closely the log-normal distribution of fresh human platelets.

A comparison of the volume distribution histogram of the platelets in fresh, human whole blood with the volume distribution histogram of a typical commercial platelet reference control made from human platelets shows that the modal point of the distribution of the commercial reference control platelet suspension is significantly lower than that of the platelets in fresh blood. In addition, the low-volume end of the histogram for the reference control material is lower than that found for the fresh platelets. This would seem to indicate that the preservation process now used in the manufacture of the reference control suspension caused significant shrinkage of platelets.

Other commercial platelet reference control preparations suffer on aging from deterioration of the volume distribution histogram characteristics as well as deterioration of other parameters. Thus, the usefulness of a given lot number of a platelet reference control or a whole blood control containing platelets can be limited by the lack of stability of the assigned value.

There appears to be an inherent incompatibility between the need to stabilize the reference control platelets for the purpose of obtaining good product shelf life and the maintenance of the size range, mean volume and log-normal size distribution histogram which are characteristic of normal platelets. The solution to the problem lies not in the pursuit of more effective ways of stabilizing "real" (human) platelets, but in substituting a surrogate which satisfies the specifications against which the product is made. Animal platelets are not useful because they are small in number, and also tend to clump together.

With the increasing use of automated devices capable of performing multiple hematological determinations and with the introduction of techniques of automated cell counting, there has been an increasing need for the development of particles which can be used either for reference control purposes or as calibrators.

Three principal types of particles heretofore have been investigated namely, human or animal cells, non-animal cells such as yeasts or pollens, and synthetic particles such as polystyrene latex. Latex particles, while capable of being manufactured to very close mean volume and size distribution specifications, present serious problems in achieving smooth, uniform suspensions. Pollens and yeasts, in addition to sharing the suspension stability problems of latex particles, suffer from lack of uniformity from batch to batch, and in some cases, lack of availability. A further requirement for the platelet component in a whole blood reference control for multi-parameter instruments is that the cells must be lysed by the lytic reagent. Latex particles and non-animal cells lack this property.

SUMMARY OF THE INVENTION

We have discovered that goats which have erythrocytes that normally fall into the low size (volume) range, react to a controlled environment by producing erythrocytes which are similar, or can be altered or blended to be similar, in number, size, and distribution to the number, size and distribution of human platelets in whole blood so as to be useful as a human platelet analog that is stable and reproducible for use as a reference control in particle analysis instruments of the Coulter type, such as the Coulter Channelyzer ®, Coulter Counter ®S-Plus, or the Thrombocounter ®, all manufactured by Coulter Electronics, Inc. of Hialeah, Fla.

In accordance with this invention goat erythrocytes are altered or blended to simulate a human platelet analog that is stable and reproducible with respect to absolute number of erythrocytes per cubic millimeter of blood, and with respect to volume and size distribution specifications. The product is designed to behave in a manner which as closely as possible simulates fresh human platelets. In addition, the product is designed to possess a feature not found in fresh normal platelets, that is a high level of stability of the parameters measured by the cell counters in which it is used. Accordingly, a standardized and stabilized goat red blood cell composition provides a suitable reference control which is useful in the enumeration of human platelets by automated means using instruments operating under the employed Coulter Principle, or by various microscopic techniques, such as illumination or phase contrast methods. The cells treated by the method disclosed herein provide an excellent system of checks and balances so necessary in hematological determinations.

The following overall procedure is employed for providing stable goat erythrocytes as a reference control for automated counting of platelets in human blood:

a. Freshly drawn blood from a goat which has been selected with respect to a controlled environment is mixed with a suitable anticoagulant, and the cellular components are suspended in an isotonic solution.
b. The specific volume of the goat cells is altered if needed, by one or both of the following techniques:
   (1) by chemical means, using a stabilizing and volume altering solution to shrink the red blood cells, and then washing the cells with a suitable wash soltuion;
   (2) by mild warming from about 20° C. to about 60° C. for about 4 to more than 120 minutes. The preferred temperature is usually 45° C.
c. The number and size distribution of the erythrocytes in the sample are determined using a particle counting instrument such as any of the Coulter ® instruments referred to above.
d. Samples from several individual goats are combined, as hereafter described, to obtain a blend for use as a reference control in which the altered cells simulate in number, size, and log normal distribution the platelets present in human whole blood.

DESCRIPTION OF THE PREFERRED EMBODIMENTS

Goat erythrocytes normally fall into the low-volume size range. It has now been found that the volume and size distribution range of the goat erythrocytes of an individual goat are infuenced by factors such as its chronological age in months, sex, hereditary factors which can be controlled by selective breeding, veterinary treatment in vivo or in vitro, phlebotomy (bleeding) which results in anemia, either induced or acquired, general health, diet, a controlled environment or pharmacological interference. By careful selection of these factors goat erythrocytes can be obtained which have a volume and size distribution close to the typical size range and volume distribution range of fresh human platelets. Such goats will have mean erythrocyte volumes only two or three times the mean volume of human platelets (seven to nine cubic microns).

These erythrocytes generally show excellent suspension stability, highly reproducible volume distribution characteristics and are readily available on a commercial scale. Goats three to nine months old are especially preferred.

The usefulness of these erythrocytes as surrogate platelets may be limited by the necessity to shrink them to within the platelet size range. Exposure of erythrocytes to hypo- or hyper-osmotic environments has the principal effect of changing the mean corpuscular volume, slightly increasing or decreasing the widths of the size distribution histograms, but only causing a trivial effect on symmetry of the size distribution histogram.

Shrinking or expansion of the cells by manipulating their osmotic environment prior to fixation has limitations due to criticality of the fixation process required to maintain stability of the altered cells. Generally one cannot shrink or swell erythrocytes more than about 30% for this purpose. Therefore, it is necessary to start with animal erythrocytes which are close in size to what will be needed finally for use as a human platelet surrogate.

The following is a specific example of preferred reagents for treating the goat cells. It will be understood that the formulations are only illustrative, and various other ingredients and proportions may be employed, in accordance with this disclosure.

Anticoagulants for Collection of Goat Blood

One or more of the following anticoagulants can be used in suitable quantity, as determined by the man skilled in the art.
1. Standard ACD (acid-citrate-dextrose)
2. Standard CPD (citrate-phosphate-dextrose)
3. Disodium EDTA (ethylenediamine tetraacetate), 2 mg/ml of blood
4. The stabilizing and volume alteration solution described below.

Stabilizing and Volume Alteration Solution (liter formulation)

Lactose: 90.0 gm
Sodium azide: 1.5 gm
Trisodium citrate dihydrate: 5.0 gm
Citric acid monohydrate: 0.1 gm
Non-ionic surfactant (Pluronic F68): 1.0 gm
Water: QS to 350 mOs/kg
  pH 6.8−7.0 Acceptable pH range 6.5−7.5
  Osm=350–360 mOsm/kg

Wash Solution (liter formulation)

Lactose: 100.00 gm
Trisodium citrate dihydrate: 2.50 gm
Citric acid monohydrate: 0.20 gm Goat cells treated by the above method are highly stable when used in a whole blood reference control. They can also be fixed for further stability when used as a free-standing platelet control.

Although goat erythrocytes normally fall into the low-volume size range, blood from any one goat demonstrates an apparently universal characteristic of erythrocytes, namely, that the volume distribution histogram is Gaussian (bell-shaped) or near-Gaussian, rather than the log-normal volume distribution which is required for accurate simulation of human platelets. However, the mathematics of non-Gaussian distribution expressed in terms of multiphasic Gaussian families is well understood. Both simple harmonic analysis and Fourrier analysis techniques have been applied to complex wave-forms for many years and it is known that virtually any distribution histogram or wave-form can be synthesized by an appropriate combination of simple symmetrical wave-forms (or histograms), each having known amplitude and frequency characteristics.

In an implementation of the present invention, the mathematics of wave-form analysis can be applied to specify the quantitative relationships of the minimum number of different goat erythrocyte populations within the small-cell colony which, when mixed together, will produce a volume distribution histogram closely approximating the volume distribution histogram of platelets in fresh normal human blood. Goat erythrocytes will give a quantity of the smaller cells sufficient to produce a log-normal distribution on the histogram. Thus the appropriate log-normal distribution of goat erythrocytes may be produced by blending multiple populations of predetermined ratios of blood from many individuals goats.

In order to produce a reference control from goat erythrocytes which is stable and reproducible so as to be useful as a human platelet analog, by manual methods, the invention will now be described, by way of example, with reference to the accompanying drawings showing population histograms in which:

FIG. 1 is a base pool of goat red cells after volume altering;

FIG. 2 is a cell pool to which goat red cells having a larger mean cell volume have been added to that of FIG. 1 to increase the rightward skewness of the curve.

FIG. 3 shows the population distribution curve when cells from a smaller mean cell volume pool are added to that of FIG. 2 to shift the distribution to a smaller mean value.

FIG. 4 shows the population distribution curve when cells from an intermediate mean cell volume pool are added to raise (increase) the mean by skewing the curve to the right, producing a log normal curve.

FIG. 5 is a population distribution curve exhibiting the log normal distribution of fresh, untreated human platelets.

From available pools of goat cells, select stabilized goat cells, that have been assayed (by channelization) and are found to be Gaussian or nearly Gaussian in cell distribution. Cell pools having mean cellular volumes between 7.5 and 12 cubic microns will be acceptable for blending. Select from these low-volume cell pools the goat cell pool having the smallest mean cell volume. In order to modify the essentially Gaussian distribution of this base pool into the desired log-normal distribution typical of platelets, it will be necessary to add to this base pool smaller amounts of cell pools having a larger mean cell volume. Compare the base pool population distribution with those of the other pools available and select a pool having a mean cell volume approximately 10 to 25 percent larger than the base pool. Add to the base pool a quantity of the cells from the selected pool which is about 10–20 percent of the cell count of the total base pool, and mix well. Measure and record the population distribution and compare with the log-normal distribution desired. Select another cell pool, if necessary, and add cells to the base pool to broaden the distribution. Remeasure and record the population distribution; then repeat the adjusting process with the same cell pool or a different cell pool in order to adjust the shape of the curve until a log-normal distribution is obtained.

Certain types of pharmacological interference tend to alter somewhat the Gaussian distribution histogram of a particular goat. For example, a microcytic anemia with an increased proportion of reticulocytes can be produced by bleeding. A skewed distribution of the erythrocytes results in a histogram which assumes more nearly a log-normal shape similar to that of fresh human platelets. It is an advantage of the foregoing manual procedure that the method is applicable starting from a specific goat cell pool, whatever the actual shape of the initial erythrocyte distribution proves to be. In some instances only a slight adjustment may be needed to adjust the curve to the desired log-normal shape to simulate the platelets of fresh normal human blood. Occasionally, no adjustment is required.

What we seek to be protected by U.S. Letters Patent is:

1. A human platelet analog for determining multiplatelet parameters comprising a blend of goat erythrocytes from several individual goats, said selection being based upon factors or controlled characteristics which produce cells having the desired mean size distribution, said goat erythrocytes having been combined and blended, as necessary, to have a size range and volume distribution close to that of human platelets, and a known number of such erythrocytes per unit volume, from which an ascertained dilution is formed to simulate the size, number and volume distribution of platelets in human whole blood, the volume distribution and known number having been determined by the use of a particle sizing and counting instrument, wherein the volume distribution histogram of said blend assumes approximately the log normal distribution of fresh platelets in human whole blood.

2. A human platelet analog according to claim 1 in which the erythrocytes are procured from goats selected with respect to at least one of: age, sex, selective breeding, a controlled environment, acquired anemia in vivo, induced anemia in vivo, and diet to have erythrocytes close to the typical size and volume distribution range of human platelets.

3. The human platelet analog of claim 1 in which the volume of the erythrocytes has been altered by heating within the range of 20° to 60° C. for 4 to more than 120 minutes.

4. The human platelet analog of claim 1 in which the volume of the erythrocytes has been altered by treatment with an aqueous solution containing lactose, sodium azide, trisodium citrate dihydrate and citric acid monohydrate, and a surfactant, said solution having a pH of 6.8 to about 7.0 and an osmolality of 350 to about 360 mOsm/kg.

5. A method for preparing a human platelet analog for determining multiplatelet parameters which comprises:
   a. Procuring goat erythrocytes which have a mean size distribution not more than about 30% greater than that of human platelets;
   b. Determining the number and mean size distribution of said erythrocytes using a particle counting instrument; and
   c. Combining samples from several individual goats, as needed, to obtain a blend of goat erythrocytes which simulate in number, size and volume distribution the platelets present in whole blood, wherein the size range and volume distribution curve of said blend assumes approximately the log normal curve of fresh platelets in human whole blood.

6. The method of claim 5 wherein said goat erythrocytes in step (a) are from goats approximately three to nine months old, whereby the said goats have erythrocytes close to the typical size and volume distribution range of human platelets.

7. The method of claim 5 wherein said goat erythrocytes in step (a) are from goats having anemia induced by phlebotomy, whereby said goats have erythrocytes close to the typical size and volume distribution range of human platelets.

8. The method of claim 5 wherein the specific volume of said erythrocytes is altered, as needed, by heating within the range of 20° to 60° C. for 4 to more than 120 minutes to cause said erythrocytes to have a specific volume which more closely resembles that of human platelets.

9. The method of claim 5 wherein the specific volume of said erythrocytes is altered, as needed, by treating with and aqueous solution containing lactose, sodium azide, trisodium citrate dihydrate and citric acid monohydrate, and a surfactant, said solution having a pH of 6.8 to about 7.0 and an osmolality of 350 to about 360 mOsm/kg to cause said erythrocytes to have a specific volume which more closely resembles that of human platelets.

10. The method of claim 5 where in step (c) the science of waveform analysis is employed to specify the quantitative relationships of a number of different goat erythrocyte cell pools which, when mixed together, will produce a volume distribution closely approximating the volume distribution of platelets in human blood.

11. The method of claim 5 wherein said combining in step (c) is accomplished by the following manual procedure:
 a. selecting, from cell pools having mean cell volumes between 7.5 and 12 cubic microns, a base cell pool having a relatively small mean cell volume;
 b. forming a modified cell pool by adding to said base cell pool, from another cell pool, 10% to about 20% of the number of cells in the base pool, said another cell pool having a mean cell volume approximately 10% to about 25% larger than the base cell pool;
 c. measuring the population distribution of said modified cell pool and comparing same with the human platelet distribution desired;
 d. selecting a different cell pool, if necessary, for adding cells to said modified cell pool to alter its population distribution;
 e. measuring the altered population distribution and comparing same with the desired human platelet distribution; and
 f. repeating steps (d) and (e) with cell pools until the resultant population distribution assumes the log normal distribution of human platelets.

* * * * *

UNITED STATES PATENT AND TRADEMARK OFFICE
CERTIFICATE OF CORRECTION

PATENT NO. : 4,264,470
DATED : Apr. 28, 1981
INVENTOR(S) : David L. Chastain, Jr., Harold R. Crews, and Stephen L. Ledis It is certified that error appears in the above—identified patent and that said Letters Patent is hereby corrected as shown below:

Column 6, lines 13 and 49, delete the word "distribution".
Column 6, line 51, amend "number and mean size distribution" to read --number, mean size and distribution--.

Signed and Sealed this

Fourth Day of May 1982

[SEAL]

Attest:

GERALD J. MOSSINGHOFF

Attesting Officer

Commissioner of Patents and Trademarks